United States Patent [19]

Black et al.

[11] Patent Number: 5,190,980
[45] Date of Patent: * Mar. 2, 1993

[54] PYROGLUTAMIC ACID ESTERS, THEIR SYNTHESIS AND USE IN TOPICAL PRODUCTS

[75] Inventors: John G. Black, Bedford; Ian R. Scott, Northamptonshire, both of England

[73] Assignee: Lever Brothers Company, Division of Conopco, Inc., New York, N.Y.

[ * ] Notice: The portion of the term of this patent subsequent to May 17, 2005 has been disclaimed.

[21] Appl. No.: 696,286

[22] Filed: Apr. 26, 1991

Related U.S. Application Data

[63] Continuation of Ser. No. 430,074, Nov. 1, 1989, abandoned, which is a continuation of Ser. No. 17,104, Feb. 19, 1987, abandoned, which is a continuation-in-part of Ser. No. 764,170, Aug. 9, 1985, Pat. No. 4,774,225.

[30] Foreign Application Priority Data

Aug. 20, 1984 [GB] United Kingdom ............... 8421112

[51] Int. Cl.$^5$ .................... A61K 7/40; A61K 7/48; C07D 207/12
[52] U.S. Cl. ................... 514/847; 424/59; 548/519; 548/534
[58] Field of Search ............... 548/534, 519; 514/422, 514/423, 847; 424/59

[56] References Cited

U.S. PATENT DOCUMENTS

Re. 29,003 10/1976 Furienmeier et al. ............. 540/340
3,839,322 10/1974 Furlenmeier et al. ............. 540/340
3,956,323 5/1976 Furlenmeier et al. .......... 540/340 X
3,957,758 5/1976 Furlenmeier et al. ............. 540/340
4,774,255 9/1988 Black et al. ...................... 514/423

FOREIGN PATENT DOCUMENTS 1377304 12/1974 United Kingdom .

OTHER PUBLICATIONS

Noller, "Chemistry of Organic Compounds", 3rd ed: 1965, p. 183.
J. G. Barrett, et al.; (1983), "J. Innest. Dermatol", 81, pp. 122-124.
I. R. Scott, et al.; (1982), "Biochimica et Biophysica Acta.", (1982), 719, pp. 110-117.
I. R. Scott-C. R. Harding and J. G. Barrett (1982) "Histidine-rich Protein of the Keratohyalin Granules", Bio. Chem.
Chemical Abstract 98:77945 (1983) (JF-A-57 91933-Pola Chemical Industries Inc.).
Hack's Chemical Dictional (4th edition) p. 25.
Webster's New Collegiate Dictionary, (1980 edition) p. 596.

Primary Examiner—Joseph Paul Brust
Attorney, Agent, or Firm—Ronald A. Koatz

[57] ABSTRACT

The invention relates to esters of pyroglutamic acid, their synthesis and their use in products for topical application to human skin as precursors of pyroglutamic acid.

10 Claims, No Drawings

PYROGLUTAMIC ACID ESTERS, THEIR SYNTHESIS AND USE IN TOPICAL PRODUCTS

This application is a continuation of U.S. Ser. No. 07/430,074, filed Nov. 1, 1989, now abandoned, which is a continuation of U.S. Ser. No. 017,104, filed Feb. 19, 1987, now abandoned, which is a continuation-in-part of U.S. Ser. No. 764,170, filed Aug. 9, 1985, now issued as U.S. Pat. No. 4,774,255.

The invention relates to esters of pyroglutamic acid, their synthesis and their use in products for topical application to human skin as precursors of pyroglutamic acid.

COMPOUNDS PER SE

Accordingly the invention provides esters of pyroglutamic acid having the structure:

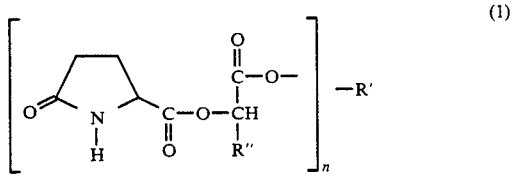 (1)

where R' and R" are the same or different and are each represented by H or the grouping:

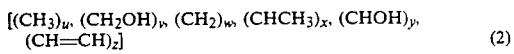 (2)

where
n is an integer of from 1 to 3
u is zero, or 1
v is zero, or an integer of from 1 to 2
w is zero, or an integer of from 1 to 21
x is zero, or an integer of from 1 to 4
y is zero, or an integer of from 1 to 2
z is zero, or an integer of from 1 to 4; and
u+v+w+x+y+z is an integer of from 1 to 22;
provided that when the subgrouping (CH=CH) is present, then the total number of carbon atoms in said grouping will be from 10 to 22;
and provided also that when R" is isobutyl, then R' is the grouping (2). The subgroups (CH$_3$, CH$_2$OH, etc.) of grouping (2) are generally interchangeable so that groups such as, for instance, isobutyl, fall within its coverage.

Examples of the grouping (2) include straight and branched chain, saturated or unsaturated aliphatic groups having from 1 to 22 carbon atoms, such as the alkyl groups:
methyl
ethyl
propyl
iso-propyl
butyl
iso-butyl
n-valeryl
iso-valeryl
n-caproyl
n-heptyl
n-caprylyl
n-capryl
lauryl
myristyl
palmityl
stearyl
arachidyl, and
behenyl;
and the C$_{10\text{-}22}$ alkenyl groups:
linoleyl
linolenyl
γ-linolenyl
arachidonyl, and
columbinyl.

As noted above, the radicals R' and R" can be olefinic in nature, i.e., they can contain a —CH=CH— group, e.g., the various linolenyl compounds, the arachidonyl and the columbinyl compound recited above.

Examples of the grouping (2) also include hydroxyalkyl groups having from 1 to 22 carbon atoms, such as:
hydroxymethyl
2-hydroxyethyl
2-hydroxy-n-propyl
3-hydroxy-n-propyl
2-hydroxy-n-butyl
3-hydroxy-n-butyl
4-hydroxy-n-butyl
5-hydroxy-n-valeryl
6-hydroxy-n-caproyl
2,3-dihydroxy-n-propyl
2,3-dihydroxy-n-butyl
12-hydroxystearyl.

It is to be understood that the above list is not exhaustive, there being many other examples of alkyl or substituted alkyl radicals expressed by the above generic grouping.

Specific examples of esters of pyroglutamic acid are:
2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy]-n-butyrate
ethyl-2-[pyroglutamoyloxy]-iso-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate
stearyl-2-[pyroglutamoyloxy]-n-propionate
12-hydroxystearyl-2-[pyroglutamoyloxy]-n-propionate
stearyl-2-[pyroglutamoyloxy]-n-stearate
palmityl-2-[pyroglutamoyloxy]-n-propionate
linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-propionate)
glyceryl mono(2-[pyroglutamoyloxy]-n-caprylate), and
glyceryl di(2-[pyroglutamoyloxy]-n-propionate).

It is to be understood that the above lists of specific examples of esters of pyroglutamic acid are not exhaustive, there being many other examples expressed by the generic structure of these esters.

SYNTHESIS OF COMPOUNDS PER SE

The invention also provides a process for the synthesis of esters of 2-pyroglutamic acid which comprises the steps of:

(i) reacting pyroglutamic acid with an ester having the structure:

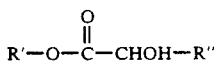
(3)

or an acid having the structure:

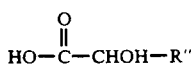
(4)

and (ii) isolating the ester of pyroglutamic acid so obtained.

It will be appreciated that when R' in the above structure is H, then the product of step (i) in the above process will be an acid having the structure:

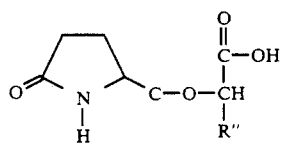
(5)

It will then be necessary to condense this acid (5) with an alcohol having the structure:

R'OH in order to obtain the ester of pyroglutamic acid according to the invention having the structure (1).

Pyroglutamic acid and the ester or acid having the structure (3) or (4), can be reacted in the dry state by heating the mixture, preferably at a pressure of less than that of atmospheric pressure. It may, however, be more convenient to react pyroglutamic acid and the ester in the presence of an organic solvent and/or a drying agent.

This aspect of the invention is illustrated by the following examples.

EXAMPLE 1

Synthesis of ethyl-2-[pyroglutamoyloxy]-propionate

Ethyl-2-[pyroglutamoyloxy]-n-propionate was prepared on a small scale refluxing tritiated pyroglutamic acid with a 10 to 20 molar excess of ethyl 2-hydroxy propionate in xylene. Anhydrous magnesium sulphate was added to remove water. After 48 hours, volatile fractions were removed by rotary evaporation and ethyl-2-[pyroglutamoyloxy]-n-propionate was isolated by thin layer chromatography on silica gel H. The structure of the isolated ester of pyroglutamic acid was confirmed by mass spectrometry and its radio chemical purity by thin layer chromatography.

EXAMPLE 2

Synthesis of ethyl-2-[pyroglutamoyloxy]-n-valerate

The procedure of Example 1 was repeated except that the ester employed was ethyl-2-hydroxy valerate.

EXAMPLE 3

Synthesis of ethyl-2-[pyroglutamoyloxy]-n-caproate

The procedure of Example 1 was repeated except that the ester employed was ethyl-2-hydroxy caproate.

EXAMPLE 4

Synthesis of ethyl-2-[pyroglutamoyloxy]- n-caprylate

The procedure of Example 1 was repeated except that the ester employed was ethyl-2-hydroxy caprylate.

EXAMPLE 5

Synthesis of iso-propyl-2-[pyroglutamoyloxy]-n-propionate 2 moles of iso-propyl lactate were refluxed with 1 mole of pyroglutamic acid in toluene with a Dean-Stark water entrainer for 72 hours. The reaction mix was cooled, filtered and rotary evaporated to leave an involatile oil containing the ester of pyroglutamic acid.

iso-Propyl-2-[pyroglutamoyloxy]-n-propionate was isolated by preparative scale high performance liquid chromatography using a hexane:ethanol gradient on a normal phase silica column. Its purity was confirmed by analytical high performance liquid chromatography and its structure by mass spectrometry.

EXAMPLE 6

Synthesis of iso-propyl-2-[pyroglutamoyloxy]-n-butyrate

The procedure described in Example 5 can be repeated using iso-propyl-2-hydroxy n-butyrate as the ester instead of iso-propyl lactate.

EXAMPLE 7

Synthesis of iso-propyl-2-[pyroglutamoyloxy]-n-caprylate

The procedure described in Example 5 was repeated except that the ester employed was iso-propyl-2-hydroxy n-caprylate.

EXAMPLE 8

Synthesis of glyceryl mono(2-[pyroglutamoyloxy]-n-caprylate)

3g of pyroglutamic acid was mixed with 3g of 2-hydroxy caprylic acid and heated at from 140° to 150° C. for three hours under 20mm pressure. The resulting 2-[pyroglutamoyloxy]-n-caprylic acid was partially purified by extraction with ethyl ether followed by separation with petroleum ether (boiling point 40°-60° C). The ester concentrated in the lower phase was dried in a stream of nitrogen.

An excess of glycerol was added to the dried 2-[pyroglutamoyloxy]-n-caprylic acid, heated at from 140° to 150° C. for 3 hours at 20mm pressure. The reaction mixture was cooled, extracted with 50% hexane, 50% ethanol and separated by preparative high performance liquid chromatography using a normal phase silica column and a gradient of hexane/ethanol. The isolated glyceryl mono-(2-[pyroglutamoyloxy]-n-caprylate) was checked for purity by analytical high performance liquid chromatography and for structure by mass spectrometry.

EXAMPLE 9

Synthesis of lauryl-2-[pyroglutamoyloxy]-n-caprylate

The procedure as described in Example 8 was repeated except that in place of glycerol, lauryl alcohol was used.

EXAMPLE 10

Synthesis of stearyl-2-[pyroglutamoyloxy]-n-caprylate

The procedure as described in Example 8 was repeated except that in place of glycerol, stearyl alcohol was used.

EXAMPLE 11

Alternative synthesis of ethyl-2-[pyroglutamoyloxy]-n-propionate

A mixture of 500 g pyroglutamic acid, 1,000 ml ethyl 2-hydroxy propionate (ethyl lactate) and 1000 ml toluene were refluxed in a Dean-Stark apparatus for 48 hours. Toluene and excess ethyl lactate were then removed by rotary evaporation and the residue distilled under vacuum (<0.5 mm Hg). The initial distillate contained residual ethyl lactate and ethyl pyroglutamic acid as a byproduct. The final distillate, a slightly yellow viscous liquid, was pure ethyl-2-[pyroglutamoyloxy]-n-propionate.

In some of the foregoing examples, tritiated pyroglutamic acid was employed as one of the starting materials to confirm the purity of the isolated 2-[pyroglutamoyloxy]- ester and to enable the fate of the tritiated ester of pyroglutamic acid to be ascertained when it is applied to skin, by locating tritiated pyroglutamic acid resulting from skin enzyme activity.

TOPICAL COMPOSITIONS

The invention further provides a composition for topical application to human skin which comprises an effective amount of from 0.01 to 99% by weight of an ester of pyroglutamic acid as herein defined together with a physiologically and cosmetically acceptable diluent. These compositions preferably comprise from 0.1 to 20%, most preferably from 0.5 to 5% by weight of the ester.

The esters of pyroglutamic acid are those as defined herein. The preferred esters for use in topical compositions according to the invention are:
2-[pyroglutamoyloxy]-propionic acid
methyl-2-[pyroglutamoyloxy]-acetate
ethyl-2-[pyroglutamoyloxy]-n-propionate
ethyl-2-[pyroglutamoyloxy]-n-butyrate
ethyl-2-[pyroglutamoyloxy]-iso-butyrate
ethyl-2-[pyroglutamoyloxy]-n-valerate
ethyl-2-[pyroglutamoyloxy]-n-caproate
ethyl-2-[pyroglutamoyloxy]-n-heptylate
ethyl-2-[pyroglutamoyloxy]-n-caprylate
ethyl-2-[pyroglutamoyloxy]-n-pelargonate
ethyl-2-[pyroglutamoyloxy]-3-hydroxybutyrate
iso-propyl-2-[pyroglutamoyloxy]-n-propionate
iso-propyl-2-[pyroglutamoyloxy]-n-caprylate
n-propyl-2-[pyroglutamoyloxy]-n-propionate
n-propyl-2-[pyroglutamoyloxy]-n-caprylate
stearyl-2-[pyroglutamoyloxy]-n-propionate
12-hydroxystearyl-2-[pyroglutamoyloxy]-n-propionate
stearyl-2-[pyroglutamoyloxy]-n-stearate
palmityl-2-[pyroglutamoyloxy]-n-propionate
linoleyl-2-[pyroglutamoyloxy]-n-propionate
linoleyl-2-[pyroglutamoyloxy]-n-caprylate
lauryl-2-[pyroglutamoyloxy]-n-caprylate
stearyl-2-[pyroglutamoyloxy]-n-caprylate
glyceryl mono(2-[pyroglutamoyloxy]-n-propionate)
glyceryl mono(2-[pyroglutamoyloxy]-n-caprylate), and
glyceryl di(2-[pyroglutamoyloxy]-n-propionate).

The physiologically and cosmetically acceptable diluent can be water, physiological saline or any suitable organic solvent in which the ester is soluble or dispersible.

The composition can be a simple solution or dispersion or a gel or a cream.

The composition according to the invention can be applied topically to human skin in order to moisturise the skin and to leave it in a soft supple condition. The composition is accordingly particularly beneficial in remoisturising dry skin or for the treatment of chapped or detergent-damaged skin. The composition can also be employed in the topical treatment of acne comedones, pimples and spots, and in the topical treatment of ichthyosis, hyperkeratosis and psoriasis, and also for the topical treatment of sunburn.

In Japanese patent KOKAI 48-82046, published November 1973, moisturising and softening compositions are disclosed, these compositions containing as effective constituents pyrrolidone carboxylates represented by the following formula:

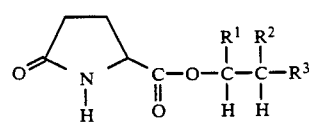

(6)

or

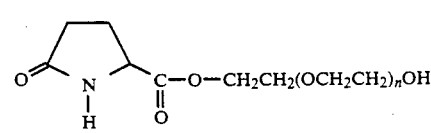

(7)

where
$R^1$ is H, $CH_3$ or $CH_2OH$
$R^2$ is H or OH
$R^3$ is $H_1$, $CH_3$, $CH_2OH$, $CH_2CH_3$, $CH(OH)CH_3$ or $CH_2CH_2OH$
n is the integer 1 or 2; and
the total number of carbon atoms in $R^1$ and $R^3$ is 1 or 2, and
the total of OH groups is 1 or 2.

MODE OF ACTION OF THE ESTERS

Pyroglutamic acid (also known as 2-pyrrolidone-5-carboxylic acid) is the principal ingredient of the "natural moisturising factor" that enables the stratum corneum of the skin to maintain a high water content despite low external humidity. Pyroglutamic acid applied topically to the skin has a temporary moisturising effect but it is easily washed away and gives no long term skin benefit.

The esters of pyroglutamic acid according to the invention are analogues of naturally occurring n-terminal pyroglutamic acid peptides. These naturally occurring peptides are substrates for the enzyme pyroglutamic acid peptidase which represents one route of pyroglutamic acid synthesis in the stratum corneum. (see: J G Barrett & I R Scott 1983 "Pyrrolidone carboxylic acid synthesis in guinea pig epidermis." J Invest. Dermatol. 81, 122). It has been discovered that the esters according to the invention readily penetrate into the stratum corneum, and there provide a substrate for this enzyme at the normal site of pyroglutamic acid synthesis, that is, inside the cells of the stratum corneum.

The amount of pyroglutamic acid produced naturally in the stratum corneum is strictly limited by the amount of a preformed protein precursor accumulated by the stratum corneum cell while it is undergoing development (see: I R Scott, C R Harding & J G Barrett (1982) "Histidine-rich protein of the keratohyalin granules : source of free amino acids, urocanic acid and pyrrolidone carboxylic acid in the stratum corneum". Biochim. Biophys-Acta 719, 110). Treatment of the skin with the esters according to the invention can therefore allow the skin to produce, using its own synthetic machinery, higher levels of pyroglutamic acid than would otherwise be possible.

Because pyroglutamic acid is thereby produced within the cells of the stratum corneum, it is very resistant to removal by washing, a significant fraction remaining after a continuous 2 hour period of water washing. This is particularly important in the treatment of dry skin.

Enzyme action on the esters according to the invention liberates not only pyroglutamic acid but also free alpha-hydroxy acids which also have proven skin benefit properties.

The invention accordingly also provides a method for the treatment of dry skin which comprises applying to skin an effective amount of a composition comprising an ester of pyroglutamic acid as herein defined.

Further, the invention also provides a method of increasing the concentration of pyroglutamic acid in skin, which comprises applying to skin an effective amount of a composition comprising an ester of pyroglutamic acid as herein defined.

By "effective amount" is meant from 0.1 to 20 mg per $cm^2$ of skin of a topical composition containing from 0.01 to 20%, preferably from 0.1 to 10% of an ester of pyroglutamic acid as herein defined. Such an amount can be applied topically to skin once, twice or three times each day.

QUANTITATIVE DATA ON EFFICACY

In an in vitro laboratory test, ethyl-2-[pyroglutamoyloxy]-n-propionate labelled with $^3H$ on the pyroglutamic acid residue was applied as a 1% solution in ethanol to newborn rat skin held in a glass cell, allowing the dermal side of the skin to be bathed in a buffered salts solution while the epidermal surface was exposed to normal atmospheric conditions. At intervals of 24 hours, samples of skin were taken and washed with continuous agitation in several changes of water at room temperature.

Interfollicular epidermis was removed from these skin pieces by "freeze scraping"—which avoids contamination of the sample by follicular tissue or material trapped within the hair follicle. The epidermis was then extracted in methanol and the soluble extract analysed by thin layer chromatography. The amount of tritiated pyroglutamic acid present was calculated as nmoles/$cm^2$ of skin surface.

The results showed that tritiated pyroglutamic acid was produced from the applied tritiated ethyl-2-[pyroglutamoyloxy]-n-propionate at a rate of 16 nmoles/$cm^2$/day for a period of at least 3 days following the single application. Of the ethyl-2-[pyroglutamoyloxy]-n-propionate applied, one quarter was converted into pyroglutamic acid over a 24 hour period, and one third of this pyroglutamic acid resisted the continuous period of 2 hours water washing.

The substantivity of tritiated pyroglutamic acid produced by the skin from tritiated ethyl-2-[pyroglutamoyloxy]-n-propionate was compared with that of tritiated pyroglutamic acid applied directly to the skin and left for the same period of time (24 hours). The percentage of the tritiated pyroglutamic acid remaining in the skin was measured over a sequence of five 20 minute water washes. The results are shown in Table 1 below:

TABLE 1

| | % pyroglutamic acid remaining in epidermis | |
|---|---|---|
| No. of washes | from ethyl-2-[pyroglutamoyloxy]-n-propionate applied topically | from pyroglutamic acid applied topically |
| 0 | 100 | 100 |
| 1 | 80 | 20 |
| 2 | 40 | 4 |
| 3 | 36 | 3 |
| 4 | 33 | 2 |
| 5 | 31 | 1 |

From these results, it can be seen that a substantial amount of pyroglutamic acid remains in the epidermis after repeated washing when that pyroglutamic acid is derived from ethyl-2-[pyroglutamoyloxy]-n-propionate according to the invention. When free pyroglutamic acid is applied to the epidermis, it is entirely washed from the tissue after a similar number of repeated washings.

The procedure described above was repeated with other tritiated esters of pyroglutamic acid according to the invention; these are listed in Table 2 below. In each case, these esters were applied to 1 $cm^2$ of newborn rat skin as 10 $\mu l$ of a 2% solution in ethanol. After 24 hours, the amount of tritiated pyroglutamic acid present in the epidermis in a form resistant to a period of 2 hours continuous washing with water was measured. The quantity of tritiated pyroglutamic acid delivered and retained by the skin in this way is recorded in Table 2 below:

TABLE 2

| Esters of tritiated pyroglutamic acid applied topically | Tritiated pyroglutamic acid delivered to epidermis: nmoles/$cm^2$/day |
|---|---|
| ethyl-2-[pyroglutamoyloxy]-n-propionate | 25 ± 5 |
| ethyl-2-[pyroglutamoyloxy]-valerate | 10.5 ± 4 |
| ethyl-2-[pyroglutamoyloxy]-n-caproate | 12 ± 4 |
| ethyl-2-[pyroglutamoyloxy]-n-caprylate | 5 ± 0.5 |

IN VITRO TESTS ON HUMAN SKIN

Initial experiments carried out on human scalp using a similar methodology to that shown above indicate that the rate of production of substantive tritiated pyroglutamic acid is comparable to that obtained using newborn rat skin, being 11 nmoles/$cm^2$/day. The level of naturally occurring pyroglutamic acid in the same samples was measured as 34 nmoles/$cm^2$. A period of three days continuous treatment with the ethyl-2-[pyroglutamoyloxy]-n-propionate can therefore double the naturally occurring level of pyroglutamic acid in the stratum corneum. Since the normal turnover time of human stratum corneum is 2-3 weeks, the stratum corneum is generating pyroglutamic acid five times faster from ethyl-2-[pyroglutamoyloxy]-n-propionate than it does from its own endogenous pyroglutamic acid precursors. The pyroglutamic acid delivered from the ester should therefore have significant beneficial effects on the moisture binding properties of the skin.

IN VIVO TESTS ON HUMAN SKIN

An in vivo study using human subjects was carried out according to the following procedure.

A solution of 5% by weight ethyl-2-[pyroglutamoyloxy]-n-propionate in 10% ethanol:90% water was applied to the upper arm over the biceps each evening for four days. A control solution of 10% ethanol:90% water was applied to the other arm. The arms were washed each evening before application. After this period of application, the arms were allowed to rest for three days with thorough washing of the arms each day.

Sellotape strips were used to sample the superficial stratum corneum on the test sites each day for a further 11 days. The arms were not washed during this period. The pyroglutamic acid content of the tapes strips was measured and expressed as n moles per mg of total protein on the strip, measured by the ninhydrin reaction after acid hydrolysis.

The results given in Table 3 below showed an increase of about 50% in the pyroglutamic acid content of the stratum corneum which persists for up to 11 days from the end of treatment. As this represents approximately the normal turnover time of the stratum corneum, the results show that treatment with ethyl-2-[pyroglutamoyloxy]-n-propionate increases the pyroglutamic acid content throughout the whole stratum corneum and not merely in the superficial layers.

TABLE 3

| Days since end of treatment | Pyroglutamic acid level in tape strip (nmoles/mg protein) | | Test: Control Ratio |
|---|---|---|---|
| | Test Site | Control Site | |
| 3 | 145 | 86 | 1.69 |
| 4 | 252 | 165 | 1.53 |
| 5 | 410 | 269 | 1.52 |
| 7 | 322 | 256 | 1.26 |
| 8 | 483 | 312 | 1.55 |
| 10 | 435 | 337 | 1.29 |
| 11 | 370 | 322 | 1.15 |
| 13 | 190 | 233 | 0.82 |

A further in vivo study using human subjects was carried out according to the following procedure.

8 volunteers applied a 5% by weight solution of ethyl-2-[pyroglutamoyloxy]-n-propionate in 10% ethanol:90% water to the back of the hand and upper arm on one side of the body and a control solution of 10% ethanol:90% water to the hand and arm on the other side. Allocation of test and control sides was random, the panellists were not informed which was the test solution.

The applications were made each evening and hands and arms were washed as normal the following day. Treatment continued for 7 days then all treated sites were thoroughly washed.

4 successive tape strips were taken from each treatment site and analysed for pyroglutamic acid and protein. Pyroglutamic acid was expressed as nmoles/mg total protein as in the previously described in vivo study.

Analysis of variance of the results showed that test and control sites differed significantly in pyroglutamic acid level (P<0.001). In the case of the hand, treatment with ethyl-2-[pyroglutamoyloxy]-n-propionate increased pyroglutamic acid level 1.75 times although there was variation in this mean value between the different strips taken from any one site. On the arm, the increase was 2.34 times and was fairly consistent from the first to the last strip.

Compositions containing esters of the invention are further illustrated by the following Examples of topical compositions suitable for application to human skin.

EXAMPLE 12

This example illustrates a high internal phase water-in-oil emulsion containing an ester of the invention.

A high internal phase water-in-oil emulsion having the following formulation was prepared:

| | % w/w |
|---|---|
| Fully hydrogenated coconut oil | 3.9 |
| 2-[pyroglutamoyloxy]-n-propionic acid | 5 |
| Brij 92* | 5 |
| Bentone 38 | 0.5 |
| Preservative | 0.3 |
| MgSO$_4$ 7H$_2$O | 0.3 |
| Butylated hydroxy toluene | 0.01 |
| Perfume | qs |
| Water | to 100 |

*Brij 92 is polyoxyethylene (2) oleyl ether.

EXAMPLE 13

This example illustrates an oil-in-water cream containing an ester of the invention.

An oil-in-water cream emulsion having the following formulation was prepared:

| | % w/w |
|---|---|
| Mineral oil | 4 |
| Ethyl-2-[pyroglutamoyloxy]-n-propionate | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol.

EXAMPLE 14

This example illustrates an alcoholic lotion containing an ester of the invention.

The lotion had the following formulation:

| | % w/w |
|---|---|
| iso-Propyl-2-[pyroglutamoyloxy]-n-propionate | 0.2 |
| Ethanol | 40 |
| Perfume | qs |
| Butylated hydroxy toluene | 0.01 |
| Water | to 100 |

EXAMPLE 15

This example illustrates an alcoholic lotion containing an ester of the invention.

The lotion had the following formulation:

|  | % w/w |
|---|---|
| Ethyl-2-[pyroglutamoyloxy]-n-caprylate | 1 |
| Dimethylsulphoxide | 10 |
| Ethanol | 40 |
| Antioxidant | 0.1 |
| Perfume | qs |
| Water | to 100 |

EXAMPLES 16 & 17

The following composition according to the invention represent lotions which can be used in the treatment of dry skin:

|  | % w/w | |
|---|---|---|
|  | 16 | 17 |
| Glyceryl mono(2-[pyroglutamoyloxy]-n-propionate) | 1.5 | — |
| Stearyl-2-[pyroglutamoyloxy]-stearate | — | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilised demineralised water | to 100 | 100 |

EXAMPLES 18 & 19

The following compositions according to the invention represent lotions which can be used in the treatment of dry skin:

|  | % w/w | |
|---|---|---|
|  | 18 | 19 |
| 12-hydroxy-stearyl-2-[pyroglutamoyloxy]-stearate | 8 | — |
| Ethyl-2-[pyroglutamoyloxy]-3-hydroxy-n-butyrate | — | 15 |
| Ethanol | 10 | 10 |
| Perfume | 0.5 | 0.5 |
| Distilled water | to 100 | 100 |

EXAMPLES 20 & 21

The following compositions according to the invention represent creams which can be used to treat skin burns:

|  | % w/w | |
|---|---|---|
|  | 20 | 21 |
| Methyl-2-[pyroglutamoyloxy]-acetate | 3 | — |
| n-propyl-2-[pyroglutamoyloxy]-n-caprylate | — | 2 |
| Cetyl alcohol | 8 | 8 |
| Mineral oil | 4 | — |
| Paraffin wax | — | 2 |
| Xanthan gum | 0.3 | 0.3 |
| Preservative | 0.4 | 0.4 |
| Perfume | qs | qs |
| Demineralised water | to 100 | 100 |

EXAMPLE 22

This example illustrates a high internal phase water-in-oil emulsion containing an ester of the invention.

A high internal phase water-in-oil emulsion having the following formulation was prepared:

|  | % w/w |
|---|---|
| Fully hydrogenated coconut oil | 3.9 |
| Ethyl-2-[pyroglutamoyloxy]-n-butyrate | 0.5 |
| Brij 92* | 5 |
| Bentone 38 | 0.5 |
| Preservative | 0.3 |
| MgSO$_4$ 7H$_2$O | 0.3 |
| Butylated hydroxy toluene | 0.01 |
| Perfume | qs |
| Water | to 100 |

*Brij 92 is polyoxyethylene (2) oleyl ether

EXAMPLE 23

This example illustrates an oil-in-water cream containing an ester of the invention.

An oil-in-water cream emulsion having the following formulation was prepared:

|  | % w/w |
|---|---|
| Mineral oil | 4 |
| Ethyl-2-[pyroglutamoyloxy]-n-valerate | 0.1 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 24

This example illustrates an alcoholic lotion containing an ester of the invention.

The lotion had the following formulation:

|  | % w/w |
|---|---|
| iso-Propyl-2-[pyroglutamoyloxy]-n-caprylate | 2 |
| Ethanol | 40 |
| Perfume | qs |
| Butylated hydroxy toluene | 0.01 |
| Water | to 100 |

EXAMPLE 25

This example illustrates an alcoholic lotion containing an ester of the invention.

The lotion had the following formulation:

|  | % w/w |
|---|---|
| Ethyl-2-[pyroglutamoyloxy]-n-caprolate | 0.2 |
| Dimethylsulphoxide | 10 |
| Ethanol | 40 |
| Antioxidant | 0.1 |
| Perfume | qs |
| Water | to 100 |

EXAMPLE 26 & 27

The following compositions according to the invention represent lotions which can be used in the treatment of dry skin:

|  | % w/w | |
|---|---|---|
|  | 26 | 27 |
| Glyceryl di(2-[pyroglutamoyloxy]-propionate) | 1.5 | — |
| Stearyl-2-[pyroglutamoyloxy]-n-caprylate | — | 0.5 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilised demineralised water | to 100 | 100 |

EXAMPLES 28 & 29

The following compositions according to the invention represent lotions which can be used in the treatment of dry skin:

|  | % w/w | |
|---|---|---|
|  | 28 | 29 |
| Stearyl-2-[pyroglutamoyloxy]-n-propionate | 0.08 | — |
| n-Propyl-2-[pyroglutamoyloxy]-n-propionate | — | 0.15 |
| Ethanol | 10 | 10 |
| Perfume | 0.5 | 0.5 |
| Distilled water | to 100 | 100 |

EXAMPLES 30 & 31

The following compositions according to the invention represent creams which can be used to treat skin burns:

|  | % w/w | |
|---|---|---|
|  | 30 | 31 |
| Ethyl-2-[pyroglutamoyloxy]-acetate | 3 | — |
| iso-Propyl-2-[pyroglutamoyloxy]-n-caprylate | — | 2 |
| Cetyl alcohol | 8 | 8 |
| Mineral oil | 4 | — |
| Paraffin wax | — | 2 |
| Xanthan gum | 0.3 | 0.3 |
| Preservative | 0.4 | 0.4 |
| Perfume | qs | qs |
| Demineralised water | to 100 | 100 |

EXAMPLE 32

This example illustrates a high internal phase water-in-oil emulsion containing an ester of the invention.

A high internal phase water-in-oil emulsion having the following formulation was prepared:

|  | % w/w |
|---|---|
| Fully hydrogenated coconut oil | 3.9 |
| Ethyl-2-[pyroglutamoyloxy]-iso-butyrate | 1 |
| Brij 92* | 5 |
| Bentone 38 | 0.5 |
| Preservative | 0.3 |
| MgSO$_4$ 7H$_2$O | 0.3 |
| Butylated hydroxy toluene | 0.01 |
| Perfume | qs |
| Water | to 100 |

*Brij 92 is polyoxyethylene (2) oleyl ether.

EXAMPLE 33

This example illustrates an oil-in-water cream containing an ester of the invention.

An oil-in-water cream emulsion having the following formulation was prepared:

|  | % w/w |
|---|---|
| Mineral oil | 4 |
| Ethyl-2-[pyroglutamoyloxy]-n-pelargonate | 5 |
| Brij 56* | 4 |
| Alfol 16RD* | 4 |
| Triethanolamine | 0.75 |
| Butane-1,3-diol | 3 |
| Xanthan gum | 0.3 |
| Preservative | 0.4 |
| Perfume | qs |
| Butylated hydroxy toluene | 0.01 |
| Water | to 100 |

*Brij 56 is cetyl alcohol POE (10)
Alfol 16RD is cetyl alcohol.

EXAMPLE 34

This example illustrates an alcoholic lotion containing an ester of the invention.

The lotion had the following formulation:

|  | % w/w |
|---|---|
| Glyceryl mono(2-[pyroglutamoyloxy]-n-caprylate) | 12 |
| Ethanol | 40 |
| Perfume | qs |
| Butylated hydroxy toluene | 0.01 |
| Water | to 100 |

EXAMPLE 35

This example illustrates an alcoholic lotion containing an ester of the invention.

The lotion had the following formulation:

|  | % w/w |
|---|---|
| Palmityl-2-[pyroglutamoyloxy]-n-propionate | 5 |
| Dimethylsulphoxide | 10 |
| Ethanol | 40 |
| Antioxidant | 0.1 |
| Perfume | qs |
| Water | to 100 |

EXAMPLES 36 & 37

The following compositions according to the invention represent lotions which can be used in the treatment of dry skin:

|  | % w/w | |
|---|---|---|
|  | 36 | 37 |
| Linoleyl-2-[pyroglutamoyloxy]-n-propionate | 15 | — |
| Stearyl-2-[pyroglutamoyloxy]-stearate | — | 10 |
| Perfume | 0.1 | 0.1 |
| Hydroxyethyl cellulose | 0.4 | 0.4 |
| Absolute ethanol | 25 | 25 |
| p-methyl benzoate | 0.2 | 0.2 |
| Sterilised demineralised water | to 100 | 100 |

EXAMPLES 38 & 39

The following compositions according to the invention represent lotions which can be used in the treatment of dry skin:

|  | % w/w | |
|---|---|---|
|  | 38 | 39 |
| Linoleyl-2-[pyroglutamoyloxy]-n-caprylate | 2 | — |
| Lauryl-2-[pyroglutamoyloxy]-n-caprylate | — | 3 |
| Ethanol | 10 | 10 |
| Perfume | 0.5 | 0.5 |
| Distilled water | to 100 | 100 |

EXAMPLES 40 & 41

The following compositions according to the invention represent creams which can be used to treat skin burns:

|  | % w/w | |
|---|---|---|
|  | 40 | 41 |
| Methyl-2-[pyroglutamoyloxy]-n-heptylate | 3 | — |
| ethyl-2-[pyroglutamoyloxy]-n-caprylate | — | 2 |
| Cetyl alcohol | 8 | 8 |
| Mineral oil | 4 | — |
| Paraffin wax | — | 2 |
| Xanthan gum | 0.3 | 0.3 |
| Preservative | 0.4 | 0.4 |
| Perfume | qs | qs |
| Demineralised water | to 100 | 100 |

We claim:

1. Esters of pyroglutamic acid having the structure:

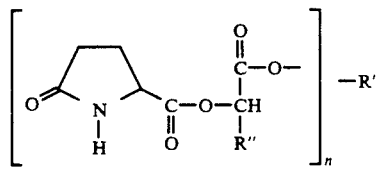

wherein n is 1 or 2; wherein R" is hydrogen, a straight or branched chain alkyl group having up to 22 carbon atoms, a straight or branched chain group selected from the group consisting of:
   hydroxymethyl
   2-hydroxyethyl
   2-hydroxy-n-propyl
   3-hydroxy-n-propyl
   2-hydroxy-n-butyl
   3-hydroxy-n-butyl
   5-hydroxy-n-valeryl
   2,3-dihydroxy-n-propyl
   2,3-dihydroxy-n-butyl, and
   12-hydroxylstearyl,
or an alkenyl group selected from the group consisting of:
   linoleyl
   linolenyl
   arachidonyl and
   columbinyl;
   and R' is defined as R" and is the same or different from R" except that it cannot be hydrogen and except that, when R" is an alkenyl group as defined above, R' must have 10 to 22 carbons.

2. The ester of claim 1, wherein R' and R" are selected from the group consisting of:
   methyl
   ethyl
   n-propyl
   iso-propyl
   n-butyl
   iso-butyl
   n-valeryl
   iso-valeryl
   n-heptyl
   n-caprylyl
   n-pelargonyl
   n-capryl
   lauryl
   myristyl
   palmityl
   stearyl
   arachidyl, and
   behenyl.

3. The ester according to claim 1, wherein said ester is ethyl-2-[pyroglutamoyloxy]-iso-butyrate.

4. A composition for topical application to human skin, which comprises an effective amount of from 0.01 to 99% by weight of:
   (a) an ester of pyroglutamic acid having the structure:

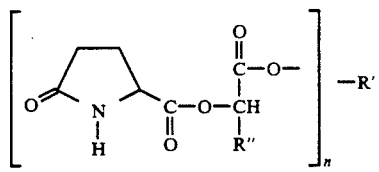

wherein n is 1 or 2; and wherein R" is hydrogen, a straight or branched chain alkyl group having up to 22 carbon atoms, a straight or branched chain group selected from the group consisting of:
   hydroxymethyl
   2-hydroxyethyl
   2-hydroxy-n-propyl
   3-hydroxy-n-propyl
   2-hydroxy-n-butyl 3-hydroxy-n-butyl
5-hydroxy-n-valeryl
2,3-dihydroxy-n-propyl
2,3-dihydroxy-n-butyl, and
12-hydroxylstearyl,
or an alkenyl group selected from the group consisting of:
linoleyl
linolenyl
arachidonyl and
columbinyl;
and R' is defined as R" and is the same or different from R" except that it cannot be hydrogen and except that, when R" is an alkenyl group as defined above, R' must have 10 to 22 carbons; and (b) a physiologically and cosmetically acceptable diluent.

5. A composition according to claim 4, wherein R' and R" are selected from the group consisting of:
methyl
ethyl
n-propyl
iso-propyl
n-butyl
iso-butyl
n-valeryl
iso-valeryl
n-heptyl
n-caprylyl
n-pelargonyl
n-capryl
lauryl
myristyl
palmityl
stearyl
arachidyl, and
behenyl.

6. A composition according to claim 4, wherein the ester is ethyl-2-[pyroglutamoyloxy]-iso-butyrate.

7. A composition according to claim 4, which further comprises a screening agent.

8. A composition according to claim 4, which is a solution dispersion, gel or cream.

9. A method of treating dry skin which comprises applying to the skin a composition for topical application to human skin, which comprises an effective amount of from 0.01 to 99% by weight of:

(a) an ester of pyroglutamic acid having the structure:

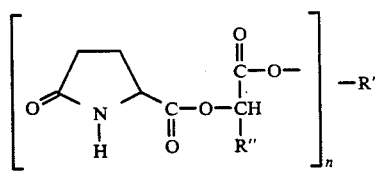

wherein n is 1 or 2; and wherein R" is hydrogen, a straight or branched chain alkyl group having up to 22 carbon atoms; a straight or branched chain group selected from the group consisting of:
hydroxymethyl
2-hydroxyethyl
2-hydroxy-n-propyl
3-hydroxy-n-propyl
2-hydroxy-n-butyl
3-hydroxy-n-butyl
5-hydroxy-n-valeryl
2,3-dihydroxy-n-propyl
2,3-dihydroxy-n-butyl, and
12-hydroxylstearyl,
or an alkenyl group, selected from the group consisting of:
linoleyl
linolenyl
arachidonyl and
columbinyl;
and R' is defined as R" and is the same or different from R" except that it cannot be hydrogen and except that, when R" is an alkenyl group as defined above, the R' must have 10 to 22 carbons; and (b) a physiologically and cosmetically acceptable diluent.

10. A method of increasing the concentration of pyroglutamic acid in skin, which comprises applying to the skin a composition for topical application to human skin which comprises an effective amount of from 0.01 to 99% by weight of:

(a) an ester of pyroglutamic acid having the structure:

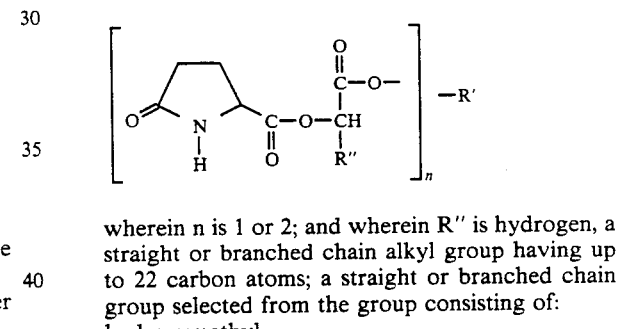

wherein n is 1 or 2; and wherein R" is hydrogen, a straight or branched chain alkyl group having up to 22 carbon atoms; a straight or branched chain group selected from the group consisting of:
hydroxymethyl
2-hydroxyethyl
2-hydroxy-n-propyl
3-hydroxy-n-propyl
2-hydroxy-n-butyl
3-hydroxy-n-butyl
5-hydroxy-n-valeryl
2,3-dihydroxy-n-propyl
2,3-dihydroxy-n-butyl, and
12-hydroxylstearyl,
or an alkenyl group selected from the group consisting of:
linoleyl
linolenyl
arachidonyl and
columbinyl;
and R' is defined as R" and is the same or different from R" except that it cannot be hydrogen and except that, when R" is an alkenyl group as defined above, R' must have 10 to 22 carbons; and (b) a physiologically and cosmetically acceptable diluent.

* * * * *